United States Patent [19]

Marsella

[11] Patent Number: 4,855,425

[45] Date of Patent: * Aug. 8, 1989

[54] PROCESS FOR THE SELECTIVE SYNTHESIS OF ETHYLENE DIAMINES

[75] Inventor: John A. Marsella, Allentown, Pa.

[73] Assignee: Air Products and Chemicals, Inc., Allentown, Pa.

[ * ] Notice: The portion of the term of this patent subsequent to Jul. 14, 2004 has been disclaimed.

[21] Appl. No.: 187,707

[22] Filed: Apr. 29, 1988

Related U.S. Application Data

[63] Continuation-in-part of Ser. No. 900,874, Aug. 27, 1986, abandoned.

[51] Int. Cl.$^4$ ............... C07D 295/02; C07C 85/06
[52] U.S. Cl. ................... 544/78; 548/524; 564/480
[58] Field of Search .................. 544/78; 564/480

[56] References Cited

U.S. PATENT DOCUMENTS

| | | | |
|---|---|---|---|
| 3,270,059 | 8/1966 | Winderl et al. | 564/480 |
| 3,708,539 | 1/1973 | Fenton | 564/480 |
| 4,487,967 | 12/1984 | Stogryn et al. | 564/474 |
| 4,745,190 | 5/1988 | Marsella | 564/480 |

FOREIGN PATENT DOCUMENTS 0034480 8/1981 European Pat. Off. .

OTHER PUBLICATIONS

R. Grigg et al, "Transition Metal-Catalysed N-Alkylation of Amines by Alcohols", J.C.S. Chem. Comm. 1981, pp. 611–612.
S. Murahashi et al, "Ruthenium Catalyzed Synthesis of Secondary or Tertiary Amines from Amines and Alcohols", Tetrahedron Letters, (vol. 23, No. 2, pp. 229–232.
A. Arcelli et al, "Selective Conversion of Primary Amines into N,N-Dimethyl-Alkyl- or N,N-Dialkylmethyl-Amines with Methanol and RuCl$_2$(Ph$_3$P)$_3$", Journal of Organometallic Chemistry (vol. 235, pp. 93–96, 1982).
Y. Watanabe et al, "Ruthenium Complex Catalyzed N-Heterocyvlization. Syntheses of N-Substituted Piperidines, Morpholines, and Piperazines from Amines and 1,5-Diols", J. Org. Chem., 50, 1365 (1985).

*Primary Examiner*—Robert W. Ramsuer
*Attorney, Agent, or Firm*—Mark L. Rodgers; William F. Marsh; James C. Simmons

[57] ABSTRACT

The present invention is a process for the selective synthesis of alkanediamines by reacting a secondary amine with an alkanediol. High conversions and high selectivity for the production of alkanediamines is achieved by carrying out the reaction in the presence of a compound or complex of ruthenium in the absence of an organic phosphine co-catalyst.

8 Claims, No Drawings

PROCESS FOR THE SELECTIVE SYNTHESIS OF ETHYLENE DIAMINES

CROSS-REFERENCE TO PARENT APPLICATION

This is a continuation-in-part of U.S. patent application Ser. No. 06/900,874, filed Aug. 27, 1986, now abandoned, the subject matter which is hereby incorporated by reference.

TECHNICAL FIELD OF THE INVENTION

The present invention relates to the catalytic synthesis of alkanediamines from alkanediols and secondary amines.

BACKGROUND OF THE INVENTION

It is known to produce certain N-substituted alkanediamines and various alkanolamines from dichloroalkanes and alkylene oxides, respectively. These starting materials are expensive and/or extremely toxic. The toxic nature of some of the alkylene oxides is a special problem for small-scale users, since the unit costs of installing safeguards and monitoring systems increase with decreasing production scale.

Previous prior art attempts aminating alkanediols have typically been limited to high temperature reactions utilizing heterogeneous catalysts. The high temperatures required in the prior art methods led to high operating pressures and low selectivities.

A limited number of prior art disclosures describe the use of homogeneous catalysts. e.g. RhH(PPh$_3$)$_4$ for the reaction of monoalcohols with amines. (See, for example, Grigg, et al, *J.C.S. Chem. Comm.*, pp 611-612 [1981]).

European Patent Publication No. 034,480 describes in general the preparation of N-alkylamine or N,N-dialkylamine by reacting a primary or secondary amine with a primary or secondary alcohol in the presence of certain noble metal catalysts, such as a salt or complex of the noble metal. The preferred example of catalyst is a rhodium hydride-triphenylphosphine complex. Although the disclosure is concerned largely with reactions involving monofunctional alcohols, there is also disclosed the reaction of a primary amine with a diol for the formation of heterocyclic ring compounds containing the amine N atom. For this purpose, the diol used should contain at least four atoms in the chain so that cyclization can occur. The publication contains no disclosure of reaction of a diol with secondary amine, wherein cyclization is not possible.

An article by Murahashi, et al. in *Tetrahedron Letters* (vol. 23, No. 2, pp. 229-232, [1982]) describes the synthesis of secondary amines by reaction of alcohols with amines in the presence of RuH$_2$(PPh$_3$)$_4$ catalyst. By the reaction of butane diol or higher alkane diols with n-hexylamine. N-heterocyclic compounds are formed.

U.S. Pat. No. 3,708,539 discloses the condensation of amines with alcohols in the presence of ruthenium or certain other noble metal catalysts introduced as halides. The process is preferably conducted in the presence of a biphilic ligand of the structure ER$_3$, wherein E may be phosphorus or arsenic. Particular examples are directed to (1) reaction of butanol with dibutylamine obtaining tributylamine; (2) using hexanol as reactant in the same manner resulted in the formation of dibutylhexylamine.

U.S. Pat. No. 4,487,967 discloses a process for selectively preparing severely sterically hindered secondary aminoether alcohols by reacting a primary amino compound with a polyalkenyl ether glycol in the presence of a hydrogenation catalyst at elevated temperatures and pressures.

Reaction of diols with ammonia or alkylamines to produce diaminoalkanes is disclosed in U.S. Pat. No. 3,270,059. The reaction is carried out in the presence of hydrogen at 150°-300° C. and at a pressure of at least 10 atmospheres, over solid catalysts which contain at least one metal from the group consisting of cobalt and nickel. When a secondary amine is employed as a reactant, tertiary diamines are obtained. Reaction of ethylene glycol with diethylamine under the conditions of the patent yields chiefly tetraethylethylene diamine and a lesser amount of diethylethanolamine.

The selective conversion of primary aliphatic amines to yield (I) N,N-dimethylalkyl- or (II) N,N-dialkylmethyl-amines by reaction with methanol in the presence of RuCl$_2$(Ph$_3$P)$_3$ catalyst, is disclosed in an article by Arcelli, et al. in the *Journal of Organometallic Chemistry* (vol. 235, pp. 93-96 [1982]). The selectivity towards the I or II type compound is controlled by choice of the amount of catalyst and the ratio of reactants.

Watanabe, et al., *J. Org. Chem.* 50, 1365 (1985) specifically teaches that RuCL$_3$×H$_2$O without a catalyst modifier is inactive as an amination catalyst for diols.

SUMMARY OF THE INVENTION

The present invention is a process for the selective synthesis of alkanediamines by reacting a secondary amine with an alkanediol at a temperature between 125°-200° C. The reaction is carried out in the presence of a catalyst consisting essentially of a compound or complex of ruthenium in the absence of an organic phosphine co-catalyst.

The present process provides for high selectivity for alkanediamines at high conversions, even in the presence of a large excess of diol.

DETAILED DESCRIPTION OF THE INVENTION

The process of the present invention achieves high selectivity of alkanediamines at high conversions by the reaction of an alkanediol with a secondary amine at high temperatures, i.e. between 125°-200° C. Improved alkanediamine selectivity, i.e. di-amination, is achieved by carrying out the amination process in the presence of a compound or complex of ruthenium in the absence of an organic phosphine co-catalyst.

Secondary amines which are useful for this reaction can be represented by the formula: HNR$_2$ in which —NR$_2$ is

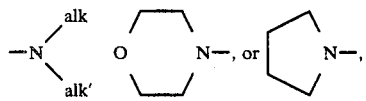

and in which "alk" and "alk'" are alkyl groups of up to 20 carbon atoms.

The alkanediols can include up to 12 carbon atoms with a linear or branched carbon skeleton. Preferably the hydroxyl groups of the alcohol functionalities should be separated by not more than two carbon atoms. Most preferably, the diols should be vicinal diols. Example of most preferred diols include ethylene glycol, 1,2-propanediol, 2,3-butanediol, 3-methyl-1,2-propanediol, 2,3-butanediol, 3-methyl-1,2-butanediol, 1,2-cyclohexanediol and 1,2-cyclododecanediol.

The concentration of the secondary amine may be in the range 0.5 to 10 moles per liter of reaction medium, and is preferably in the range of 1 to 5 mols/liter. The catalyst concentration may be generally in the range of $10^{-4}$ to $10^{-1}$ mols per liter of reaction medium, and preferably $10^{-3}$ to $10^{-2}$ mols/liter.

The catalysts which can be used in the present reaction consist essentially of a ruthenium compound or complex in the absence of an organic phosphine co-catalyst. Specific examples of ruthenium compounds or complexes which can be used for this reaction and which favor alkanediamine formation include: $RuCl_3 \times H_2O$, $Ru(NH_3)_6Cl_3$, $K_2(RuCl_5)_2O$, $Ru(NO)Cl_3$, $K_2RuCl_5$, $K_2RuCl_6$, $Ru(NH_3)_6$, $Cl_2$, $K_2RuO_4$, $RuCl_2(DMSO)_4$, "Ruthenium Red" (ammoniated ruthenium oxychloride), anhydrous $RuCl_3$, etc.

The catalysts employed in the practice of the invention, without being bound to any particular theory, apparently function as homogeneous catalysts, since they are at least partially dissolved in the reaction medium. As a result, such catalysts yield a more selective product distribution than that obtained using heterogeneous catalysts. Improved selectivity and high conversion are achieved at temperatures at which prior processes typically obtained both poor selectivity and poor conversion., i.e., 125°-200° C. and preferably between 150°-200° C.

The process is preferably carried out at autogenous pressure without requiring addition of hydrogen to the system, although hydrogen may be employed, if desired. Additionally, by the practice of the present invention, the selective synthesis of alkanediamines is made possible utilizing readily available and relatively low toxicity starting materials.

The exact composition and structure of the active catalyst species promoting the reaction is not clear since the form in which the catalyst is introduced may function merely as a precursor to the active structure formed in the medium under reaction conditions. While carbonyl complexes have been observed in reaction mixtures, the use of isolated neutral carbonyl complexes of ruthenium, as such catalyst precursors, were found to lead to lower catalytic activity.

The process of the invention may be carried out in the presence of added solvents or diluents, among which are preferred; N-methylpyrrolidinone, N,N-dimethylacetamide, dimethylsulfoxide (DMSO), water, 1,2-dimethoxyethane.

The present process typically exhibits higher selectivity toward alkanediamines at high conversions than prior art processes using heterogeneous transition metal catalysts, such as Example 6 of U.S. Pat. No. 3,270,059. The alkanediamines produced by the present process are useful as urethane catalysts, complexing agents, anti-corrosion agents and in other applications.

Several operating examples of the present process were carried out and are described below. These examples are only meant to illustrate the present invention and are not meant to be limiting.

The product distributions from the operating examples are reported as a selectivity coefficient (r) which is defined as:

$$r = \frac{Yd}{Ym + Yd}$$

where
Ym = yield of mono-aminated product(s)
Yd = yield of diaminated product(s)

A selectivity coefficient (r) of 0.5 indicates a 50/50 mixture (on an equivalent nitrogen basis) of mono- and di- aminated products, with a value of $r > 0.5$ indicating more diaminated product, and a value $r < 0.5$ indicating more mono-aminated product.

EXAMPLE 1

A 22 ml stainless steel Parr bomb reactor was charged with 5.5 g ethylene glycol (88.6 mmol), 1.0 g morpholine (11.5 mmol), 42 mg $RuCl_3 \times H_2O$ ($1.7 \times 10^{-4}$ mol) 0.52 g N-methylpyrrolidone (as internal standard) and a magnetic stirring bar in a nitrogen-filled glove box. The bomb was sealed and placed in a previously-heated oil bath with stirring. After heating for 2.5 h at 150° C. the reactor pressure was 20 psig. At this point, the bomb was cooled to room temperature at which point the pressure stood at 6 psig. The reactor was vented, opened, and the contents analyzed by GLC. The conversion of morpholine was 100% with yields of hydroxyethylmorpholine and bismorpholinoethane being 17% and 79%, respectively (r = 0.82).

This example demonstrates that $RuCl \times H_2O$ is an effective catalyst for the amination of a diol with a secondary amine without requiring an organic phosphine co-catalyst. Additionally, di-amination strongly dominated despite the fact that ethylene glycol was present in large excess relative to morpholine.

EXAMPLE 2

The procedure of Example 1 was repeated except that a temperature of 180° C. was used. After heating for 2.5 h, the reactor pressure was 39 psig. Two runs were carried out under these conditions with run 1 using $RuCl_2 \times H_2O$ as the catalyst, and a comparative run, run 2, using $RuCl_2(PPh_3)_3$ as the catalyst. The results of these two runs are reported below.

Run 1

42 mg $RuCl_3 \times H_2O$ ($1.7 \times 10^{-4}$ mol) catalyst was used and the products were analyzed by GLC. Product analysis indicated 0.05 g morpholine (95% conversion), 0.10 g hydroxyethylmorpholine (7% selectivity) and 0.84 g bismorpholinoethane (76% selectivity) (r = 0.92).

Run 2 (comparative)

130 mg $RuCl_2(PPh_3)_3$ ($1.4 \times 10^{-4}$ mol) catalyst was used in place of the $RuCl_3 \times H_2O$ in run 1. GLC product analysis indicated a 100% morpholine conversion with yields of hydroxyethylmorpholine and bismorpholinoethane being 43.7% and 50.8%, respectively (r = 0.54).

The comparative runs of Example 2 clearly indicate the selectivity for di-aminated products is greatly increased by using a ruthenium complex catalyst without an organic phosphine co-catalyst. This is totally unexpected in view of U.S. Pat. No. 3,708,539, which indicates that there is little difference between ruthenium chloride without phosphine co-catalysts and phosphine complexes of ruthenium chloride for reactions of monoalcohols with amines.

Additionally, unlike the teachings of Watanabe, et al., which specifically state that $RuCl_3 \times H_2O$ is inactive as an amination catalyst for diols, the process of the present invention achieves improved selectivity at high conversion for the amination of diols. Watanabe, et al. specifically state at p. 1366 in the above-cited article that the catalytic synthesis of N-substituted piperdine, morpholine, and piperazine derivatives from primary amines and 1,5-diols, such as 1,5-pentanediol, diethylene glycol and ethanolamines, is controlled by phosphine ligands coordinated to the ruthenium catalyst. Several examples, as reported in Tables II and III of the Watanabe article, specifically show a 0% alkanediamine product yield when a ruthenium catalyst was used without a phosphine ligand.

EXAMPLE 3

The procedure described in Example 1 was used to charge the reactor with 0.41 g $RuCl_3 \times H_2O$ ($1.8 \times 10^{-4}$ mol), 0.54 g dimethylamine ($1.2 \times 10^{-2}$ mol), 5.5 g 1,2-propanediol ($7.2 \times 10^{-2}$ mol) and 0.51 g N-methylpyrrolidone. The reactor was heated at 180° C. for 2.5 hours during which time the operating pressure rose to 98 psig. On cooling, the pressure fell to 30 psig. Analysis showed a dimethylamine conversion of 95% with selectivities being 26% N,N,N',N'-tetramethyl-1,2-diaminopropane, 39% 1-(dimethylamino)-2-propanol and 8% 2-(dimethylamino)-1-propanol (r=0.36). In a similar run with $RuCl_3(PPh_3)_3$ as catalyst, an r value of 0.12 was obtained, thus showing a significant increase in selectivity to diamine by running the reaction in the absence of triphenylphosphine, even when the overall reaction is highly selective toward mono-amination.

Having thus described the present invention, what is now deemed appropriate for Letters Patent is set out in the following appended claims.

What is claimed is:

1. A process for the selective synthesis of bismorpholino ethane or N,N,N',N'-tetramethyl-1-2-diaminopropane by the reaction of a secondary amine with ethyleneglycol or 1,2-propanediol, said process comprising: carrying out said reaction at a temperature between 125°–200° C. in the presence of a catalyst consisting essentially of $RuCl_3 \times H_2O$ in the absence of an organic phosphine co-catalyst.

2. The process in accordance with claim 1 wherein said reaction is carried out at autogenous pressure without the addition of hydrogen.

3. The process in accordance with claim 1 wherein hydrogen is added to the reaction mixture.

4. The process in accordance with claim 1 wherein said reaction is carried out in the presence of an added solvent.

5. The process in accordance with claim 4 wherein said solvent is selected from the group consisting of N-methylpyrrolidinone, N,N-dimethylacetamide, dimethylsulfoxide, water, 1,2-dimethoxyethane and mixtures thereof.

6. The process in accordance with claim 1 wherein the concentration of the secondary amine is in the range of 0.5 to 10 moles per liter of reaction medium.

7. The process in accordance with claim 1 wherein the ruthenium complex is present in a concentration in the range of $10^{-4}$ to $10^{-1}$ moles per liter of reaction medium.

8. The process in accordance with claim 1 wherein said amination takes place in the liquid phase.

* * * * *